US007582287B2

(12) United States Patent
Chandrasekher et al.

(10) Patent No.: US 7,582,287 B2
(45) Date of Patent: Sep. 1, 2009

(54) METHOD FOR TREATING CERVICAL CANCER

(75) Inventors: Yasmin A. Chandrasekher, Mercer Island, WA (US); Patricia A. McKernan, Seattle, WA (US)

(73) Assignee: Zymogenetics, Inc., Seattle, WA (US)

(*) Notice: Subject to any disclaimer, the term of this patent is extended or adjusted under 35 U.S.C. 154(b) by 434 days.

(21) Appl. No.: 10/321,163

(22) Filed: Dec. 17, 2002

(65) Prior Publication Data
US 2003/0161811 A1 Aug. 28, 2003

Related U.S. Application Data

(60) Provisional application No. 60/341,783, filed on Dec. 17, 2001.

(51) Int. Cl.
*A61K 38/19* (2006.01)
(52) U.S. Cl. .................................................... 424/85.1
(58) Field of Classification Search ........................ None
See application file for complete search history.

(56) References Cited

U.S. PATENT DOCUMENTS

| 5,723,299 | A | 3/1998 | Bell et al. ................ 435/7.1 |
| 5,789,192 | A | 8/1998 | Moore et al. ............. 435/69.1 |
| 5,843,725 | A | 12/1998 | Sledziewski et al. ....... 435/69.7 |
| 5,945,511 | A | 8/1999 | Lok et al. ................. 530/350 |
| 5,985,614 | A | 11/1999 | Rosen et al. ............. 435/69.52 |
| 6,020,163 | A | 2/2000 | Conklin ................... 435/69.1 |
| 6,486,301 | B1 | 11/2002 | Ebner et al. .............. 530/351 |
| 6,576,743 | B1 | 6/2003 | Conklin et al. ............ 530/351 |
| 6,610,286 | B2 | 8/2003 | Thompson et al. ........ 424/85.2 |
| 2002/0042366 | A1 | 4/2002 | Thompson et al. ............ 514/12 |

FOREIGN PATENT DOCUMENTS

| WO | WO94/13801 | 6/1994 |
| WO | WO99/03982 | 1/1999 |
| WO | WO99/07740 | 2/1999 |
| WO | WO99/07848 | 2/1999 |
| WO | WO99/27103 | 6/1999 |
| WO | WO99/37772 | 7/1999 |
| WO | WO99/46281 | 9/1999 |
| WO | WO99/46379 | 9/1999 |
| WO | WO99/61630 | 12/1999 |
| WO | WO00/12708 | 3/2000 |
| WO | WO 00/15264 | 3/2000 |
| WO | WO00/39161 | 7/2000 |
| WO | WO00/42189 | 7/2000 |
| WO | WO 00/42189 | * 7/2000 |
| WO | WO00/73457 | 12/2000 |
| WO | WO00/78961 | 12/2000 |
| WO | WO01/12672 | 2/2001 |
| WO | WO01/46261 | 6/2001 |
| WO | WO02/12345 | 2/2002 |
| WO | WO02/058724 | 8/2002 |
| WO | WO02/070001 | 9/2002 |
| WO | WO02/072607 | 9/2002 |
| WO | WO03/039444 | 5/2003 |
| WO | WO03/051384 | 6/2003 |
| WO | WO2004/085475 | 10/2004 |

OTHER PUBLICATIONS

Freshney (Culture of Animal Cells, A Manual of Basic Technique, Alan R. Liss, Inc., 1983, New York, p. 4.*
Dermer (Bio/Technology, 1994, 12:320).*
Gura (Science, v278, 1997, pp. 1041-1042).*
Shi et al (J. Biol Chem Jun. 2000;275(25):19167-19176).*
Rose (Cancer J. Mar.-Apr. 2001;7(2):86-92).*
Clerici et al J. Natl. Can. Inst. 1997; 89(3):245-250.*
Abbas et al., "Cellular and Molecular Immunology", 4th Ed., pp. 519-520, W.B. Saunders Company, 2000.
Albert et al., "Molecular Biology of the Cell," 3rd Ed., pp. 156-159, Garland Publishing, Inc., 1994.
Asadullah et al., *Arch Dermatol 138*:1189-1196, 2002.
Asadullah et al., *Pharmacol Rev. 55*(2):241-269, 2003.
Blumberg et al., *Cell 104*:9-19, 2001.
Cameron et al., "Cytokines and Chemokines in Autoimmune Disease," pp. 8-32, Eurekah.com and Klawer Academic/Plenum Publishers, 2003.
Conti et al., *Immunology Letters 88*:171-174, 2003.
Cunningham et al., *Science 244*:1081-1805, 1989.
Davis et al., *Cell 87*:1161-1169, 1996.
De Groot-Kruseman et al., *J. Interferon & Cytokine Research 22*(Suppl. 1):S-97, Abstract P-2-1, 2002.
Dumoutier et al., *Eur. Cytokin Netw 13*(2):5-15, 2002.
Dumoutier et al., *J. Immunol. 167*:3545-3549, 2001.
Dynan et al., *Nature 316*:774-778; 1985.
Fickenscher et al., *Trends in Immunology 23*(2):89-96, 2002.
George et al., "Macromolecular Sequencing & Synthesis," pp. 127-149, Ch. 12, Alan R. Liss, Inc., 1988.
Gröne, *Veterinary Immunol. And Immunopathal. 88*:1-12, 2002.
Harlow et al., "Antibodies A Laboratory Manual," p. 76, Ch. 5, Cold Springs Harbor Laboratory, 1988.
He et al., *J. Interferon & Cytokine Research 22*(Suppl. 1):S-97, Abstract P-1-23, 2002.
Henikoff et al., *Proc. Nat. Acad. Sci. USA 89*:10915-10919, 1992.
Hosoi et al., *The 75th Annual Meeting, Department of Pharmacology*, Kumamoto University, p. 89P, Abstract P-112, 2002.
Kotenko, *Cytokine & Growth Factor Reviews 13*:223-240, 2002.
Kotenko et al., *J. Biol. Chem. 276*(4):2725-2732, 2001.
Kotenko et al., *Oncogone 19*:2557-2565, 2000.
Kunz et al., *J. Interferon & Cytokine Research 22*(Suppl. 1):S-97-S-98, Abstract P-2-3, 2002.
Last et al., *J. Investigative Dermatology 119*(1):325, Abstract 707, 2002.
Liu et al., *Blood 100*(11):189a-190a, Abstract #710, 2002.

(Continued)

*Primary Examiner*—Christopher H Yaen
(74) *Attorney, Agent, or Firm*—Marshall, Gerstein & Borun LLP

(57) ABSTRACT

Use of Interleukin-20 for treating cervical cancer or cells infected with human papilloma virus. IL-20 can be administered alone or in conjunction with radiation or chemotherapeutic agents or surgical excision of the involved cells or lesions.

15 Claims, No Drawings

OTHER PUBLICATIONS

Liu et al., *Journal of Immunology* 152:1821-1829, 1994.
Liu et al., *Blood* 102(9):3206-3209; 2003.
Lutfalla et al., *Genomics* 16:366-373, 1993.
Lutfalla et al., *J. Mol. Evolution* 41:338-344, 1995
Lillehoj et al., "Antibody Techniques," pp. 291-305, Ch. 13, Academic Press, Inc., 1994.
McKinnon et al., *Drug News and Perspectives* 9(7):389-398, 1996.
Merck Manual 17$^{th}$ Ed., pp. 920-925.
Mohler et al., *FASB J. US Fed of American Soc. For Experimental Biology* 6(4):A1123, 1992.
Musso et al., *J. Interferon & Cytokine Research* 22(Suppl. 1):S-98, Abstract P-2-4, 2002.
Ozaki et al., *J. Biol. Chem.0* 277(33):29355-29358, 2002.
Parrish-Novak et al., *J. Biol. Chem* 277(49):47517-47523, 2002.
Parrish-Novak et al., *J. Interferon & Cytokine Research* 22(Suppl. 1):S-46, Abstract W-1-5, 2002.
Pirhonen et al., *J. Interferon & Cytokine Research* 22(Suppl. 1): S-98, Abstract P-2-6, 2002.
Ramesh et. al., *Cancer Gene Therapy*: S3, Abstract 008, 2002.
Rich et al., *Curr Biol.* 11(13):R531-R534, 2001.
Rich, *Expert Opin. Ther. Targets* 7(2):165-174, 2003.
Rohovsky et al., "Growth Factors and Wound Healing" pp. 8-26, Ch. 2; Springer, 1997.
Roitt et al., "Immunology," 4$^{th}$ Ed., pp. 28.10-28.12, Mosby, 1996.
Rose-John, *Acta Biochimica Polonica* 50(3):603-611, 2003.
Salazar et al., *Eur. J. of Clin. Invest.* 31(12):1070-1077, 2001.
Slavin, *J. Immunol. Immunopharmacol* 17(1):25-29, 1997.
Stolina et al., *J. Interferon & Cytokine Research* 22(Suppl. 1):S-98-S-99, Abstract P-2-7, 2002.
Strengell et al., *J. Interferon & Cytokine Research* 22(Suppl. 1):S-99, Abstract P-2-8, 2002.
Tachiiri et al., *Genes and Immunity* 4: 153-159, 2003.
Vandenbroeck et al., *J. Biol. Chem.* 277(28):25668-25676, 2002.
Volk et al., *Trends in Immunology* 22(8):414-417, 2001.
Walter, *Immunologic Res.* 26(1-3):303-308, 2002.
Whitters et al., *J. Interferon & Cytokine Research* 22(Suppl. 1):S-99-S-100, Abstract P-2-11, 2002.
Witek et al., *J. Interferon & Cytokine Research* 22(Suppl. 1):S-100, Abstract P-2-12, 2002.
Wolk et al., *J. Immunol.* 168:5397-5402, 2002.
Wuyts et al., *Eur J. Biochem.* 260:421-429, 1999.
Xie et al., *J. Biol. Chem.* 275(40):31335-31339, 2000.
Xu et al., *Proc. Nat. Acad. Sci. USA.* 98(17):9511-9516, 2001.
EST from Incyte Pharmaceuticals Inc., INC1429789, 1996.
EST from Incyte Pharmaceuticals Inc., INC1922140, 1996.
EST from Incyte Pharmaceuticals Inc., INC1923851, 1996.
EST from Incyte Pharmaceuticals Inc., INC2119350, 1996.
EST from Incyte Pharmaceuticals Inc., INC2270605, 1996.
EST from Incyte Pharmaceuticals Inc., INC2699058, 1997.
EST from Incyte Pharmaceuticals Inc., INC2701079, 1997.
EST from Incyte Pharmaceuticals Inc., INC2720417, 1997.
EST from Incyte Pharmaceuticals Inc., INC2763478, 1997.
EST from Incyte Pharmaceuticals Inc., INC3256488, 1997.
EST from Incyte Pharmaceuticals Inc., INC3257185, 1997.
EST from Incyte Pharmaceuticals Inc., INC3316826, 1997.
EST from Incyte Pharmaceuticals Inc., INC3376533, 1997.
EST from Incyte Pharmaceuticals Inc., INC357666, 1995.
EST from Incyte Pharmaceuticals Inc., INC4304592, 1998.
EST from Incyte Pharmaceuticals Inc., INC758088, 1996.
EST from Incyte Pharmaceuticals Inc., INC819592, 1996.
EST from Incyte Pharmaceuticals Inc., INC904360, 1996.
EST from TIGR Tentative Human Consensus, THC174656, 1997.
EST from TIGR Tentative Human Consensus, THC197949, 1997.
EST from TIGR Tentative Human Consensus, THC215509, 1997.
GenBank Accession No. AA018585, 1995.
GenBank Accession No. AA018749, 1995.
GenBank Accession No. AA035594, 1995.
GenBank Accession No. AA132964, 1995.
GenBank Accession No. AA134881, 1995.
GenBank Accession No. AA135185, 1995.
GenBank Accession No. AA135300, 1995.
GenBank Accession No. AA299011, 1995.
GenBank Accession No. AA412292, 1997.
GenBank Accession No. AA470014, 1997.
GenBank Accession No. AA494556, 1997.
GenBank Accession No. AA514541, 1997.
GenBank Accession No. AA516435, 1997.
GenBank Accession No. AA528216, 1997.
GenBank Accession No. AA583432, 1997.
GenBank Accession No. AA632915, 1997.
GenBank Accession No. H17201, 1995.
GenBank Accession No. H17978, 1995.
GenBank Accession No. N62509, 1995.
GenBank Accession No. N79409, 1995.
GenBank Accession No. R14678, 1995.
GenBank Accession No. R42401, 1995.
GenBank Accession No. T70354, 1995.
GenBank Accession No. T70439, 1995.
International Search Report from PCT/US02/40309.
Supplementary Partial European Search Report from counterpart European Application No. EP 02 80 518.1.
Supplementary European Search Report from counterpart European Application No. EP 02 80 518.1.
Article 94(3) EPC Communication dated Dec. 13, 2007.
Article 94(3) EPC Communication dated Dec. 9, 2008.

\* cited by examiner

METHOD FOR TREATING CERVICAL CANCER

This claims the benefit under 35 U.S.C. § 119 (e) of U.S. Provisional Application No. 60/341,783 filed on Dec. 17, 2001.

BACKGROUND OF THE INVENTION

According to the American Cancer Society, 12,800 new cases of invasive cervical cancer would be diagnosed in the United States in 1999. During the same year, 4800 patients were expected to die of the disease. This represents approximately 1.8% of all cancer deaths in women and 18% of gynecological cancer deaths. However, for women aged 20 to 39 years of age, cervical cancer is the second leading cause of cancer deaths. Molecular and epidemiologic studies have demonstrated a strong relationship between human papillomavirus (HPV), cervical intraepithelial neoplasia, (CIN), and invasive carcinoma of the cervix. Thus, there is a need to develop new therapeutic entities for the treatment of human papillomavirus infection, cervical intraepithelial neoplasia and carcinoma of the cervix.

DESCRIPTION OF THE INVENTION

The present invention fills this need by administering interleukin-20 (IL-20) to a mammalian having cervical cancer. IL-20 can also be used to treat a human papillomavirus infection. The present invention also provides a method for inhibiting the growth of cervical cancer cells by bringing IL-20 into contact with said cancerous cervical cells. Interleukin-20 (formally called Zcyto10) can be produced according to the method described in International Patent Application No. PCT/US98/25228 filed on Nov. 25, 1998. The human IL-20 polypeptide is comprised of a sequence of 176 amino acids with the initial Met as shown in SEQ ID NO:1 and SEQ ID NO:2. It is believed that amino residues 1-24 are signal sequence, and the mature IL-20 polypeptide is represented by the amino acid sequence comprised of residues 25, a leucine, through amino acid residue 176, a glutamic acid residue, also defined by SEQ ID NO:12. Another embodiment of the present invention is defined by the sequences of SEQ ID NO:3 and SEQ ID NO:4. The polypeptide of SEQ ID NO:4 is comprised of 151 amino acid residues wherein amino acids 1-24 comprise a signal sequence and the mature sequence is comprised of amino acid residues 25, a leucine, through amino acid 151 a glutamic acid, also defined by SEQ ID NO:13. Another active variant is comprised of amino acid residues 33, a cysteine, through amino acid residue 176 of SEQ ID NO:2. This variant is also defined by SEQ ID NO:26.

Mouse IL-20 is also a polypeptide comprised of 176 amino acid residues as defined by SEQ ID NOs:18 and 19. Mouse IL-20 has a signal sequence extending from amino acid residue 1, a methionine, extending to and including amino acid residue 24, a glycine of SEQ ID NO:19. Thus, the mature mouse IL-20 extends from amino acid residue 25, a leucine, to and including amino acid residue 176 a leucine of SEQ ID NO:19, also defined by SEQ ID NO:20. Another active variant is believed to extend from amino acid 33, a cysteine, through amino acid 176, of SEQ ID NO:19. This variant is also defined by SEQ ID NO:25.

A variant of mouse IL-20 is defined by SEQ ID NOs:33 and 34. This variant is 154 amino acid residues in length and has a signal sequence extending from amino acid residue 1, a methionine, to and including amino acid residue 24, a glycine, of SEQ ID NO:34. Thus, the mature sequence extends from amino acid residue 25, a leucine, to and including amino acid residue 154, a leucine, of SEQ ID NO:34. The mature sequence is also defined by SEQ ID NO:35.

Pathology of Cervical Cancer

Cervical dysplasia cells and cervical intraepithelial neoplasia (CIN) cells develop into invasive cervical cancer over a number of years. CIN grades I, II and III correspond to mild, moderate, and severe cervical dysplasia. CIN III, which includes severe dysplasia and carcinoma in situ, is unlikely to regress spontaneously and, if untreated, may eventually penetrate the basement membrane, becoming invasive carcinoma. Squamous cell carcinoma accounts for 80 to 85% of all cervical cancers; adenocarcinomas account for most of the rest. Invasive cervical cancer usually spreads by direct extension into surrounding tissues and the vagina or via the lymphatics to the pelvic and para-aortic lymph nodes drained by the cervix. Hematologic spread is possible.

Symptoms, Signs and Diagnosis of Cervical Cancer

CIN is usually asymptomatic and discovered because of an abnormal Pap smear. Patients with early-stage cervical cancer usually present with irregular vaginal bleeding, which is most often postcoital, but intermenstrual bleeding or menometrorrhagia may occur. Patients with larger cervical cancers or advanced-stage disease may present with foul-smelling vaginal discharge, abnormal vaginal bleeding, or pelvic pain. Obstructive uropathy, back pain, and leg swelling are manifestations of late-stage disease. Suspicious lesions, generally first detected by a Pap smear are biopsied. If clinical disease is invasive, staging is performed on the basis of the physical examination, with a metastatic survey including cystoscopy, sigmoidoscopy, IV pyelography, chest x-ray, and skeletal x-rays.

Treatment of Cervical Cancer with IL-20

Cervical cancer can be treated by administration of IL-20 to a female mammal, particularly a human female, afflicted with the disease. IL-20 can be administered intralesionally, or intramuscularly for localized disease. For metastatic disease, IL-20 can also be administered by intraperitoneal administration including intravenous administration. IL-20 can be administered alone or in conjunction with standard therapies such as surgery, radiation or other chemotherapeutic agents such as bleomycin, chlorambucil, epirubicin, 5-fluorouracil, ifosfamide, mitomycin, methotrexate, vincristine, cisplatin and vinblastine.

Use of Interleukin-20 to Treat Cells Infected with the Human Papillomavirus/Genital Warts Cells infected with the human papillomavirus (HPV) can be treated with IL-20 to inhibit the proliferation of the virus. Anogenital warts caused by HPV type 6, 11, 16, 18, 31, 33 and 35 are transmitted sexually and have an incubation period of 1 to 6 months. Endocervical wart infections caused by type 16 or 18 have been implicated as a cause of cervical intraepithelial neoplasia and cervical cancer. HPV types 16 and 18 generally do no not cause external genital warts, which are usually caused by types 6 and 11.

Symptoms, Signs and Diagnosis

Genital warts usually appear as soft, moist, minute pink or gray polyps that enlarge, may become pedunculated, and are usually found in clusters. The surfaces resemble the surface of cauliflower. In men they occur most commonly on warm, moist surfaces in the subpreputial area, on the coronal sulcus, within the urethral meatus, and on the penile shaft. In women, the vulva, the vaginal wall, the cervix, and the perineum may become involved. They are particularly common in the perianal region and rectum in homosexual men. Growth rates vary, but pregnancy, immunosuppression, or maceration of the skin may accelerate both the growth of individual lesions and their spread. Genital warts usually can be identified by their appearance but must be differentiated from the flat-topped condyloma lata of secondary syphilis. Biopsies of a typical or persistent warts may be necessary to exclude carcinoma.

IL-20 can be administered directly into lesions containing cells infected with HPV alone or with standard therapies such as interferon alpha or interferon beta both of which are commercially available. Interferon alpha is available from Schering Corporation of Kenilworth, N.J. and is called INTRON A®. Interferon beta is produced by Biogen of Cambridge, Mass. and is called AVONEX®. IL-20 can also be administered with other standard therapies for treating HPV including antimitotics such as podophyllotoxin, podophyllin, or 5-fluorouracil; caustics such as trichloroacetic acid; or interferon inducers such as imiquimod.

The quantities of IL-20 for effective therapy will depend upon many different factors, including means of administration, target site, physiological state of the patient, and other medications administered. Thus, treatment dosages should be titrated to optimize safety and efficacy. Typically, dosages used in vitro may provide useful guidance in the amounts useful for in vivo administration of these reagents. Animal testing of effective doses for treatment of particular disorders will provide further predictive indication of human dosage. Methods for administration include, intravenous, peritoneal, intramuscular, or intralesional. Pharmaceutically acceptable carriers will include water, saline, buffers to name just a few. Dosage ranges would ordinarily be expected from 1 μg to 1000 μg per kilogram of body weight per day. However, the doses may be higher or lower as can be determined by a medical doctor with ordinary skill in the art. Excipients and stabilizers can possible be added. These include glycine, histidine, glutamate, aspartate, sugars, sucrose, trehalose, galactose sorbitol, arginine, D-and/or L0amino acids, sugar alcohols, lactose, maltose, threonine, lysine, methionine, isoleucine, a surface active agent such as TWEEN 80, TWEEN 20, polyethylene glycol (PEG) (particularly those PEGs having molecular weights between 1000 and 35000 Da), cetyl alcohol, polyvinylpyrrolidone, polyvinyl alcohol, lanolin alcohol and sorbitan. A reducing agent may be included, such as cysteine, N-acetyl-cysteine, and thioglycerol. For a complete discussion of drug formulations and dosage ranges see *Remington's Pharmaceutical Sciences,* 18th Ed., (Mack Publishing Co., Easton, Pa., 1996), and *Goodman and Gilman's: The Pharmacological Bases of Therapeutics,* 9th Ed. (Pergamon Press 1996).

IL-20 can also me administered in conjunction with other treatments for cervical cancer such as radiation and chemotherapy. Examples of chemotherapeutic agents include bleomycin, chlorambucil, epirubicin, 5-fluorouracil, ifosfamide, mitomycin, methotrexate, vincristine, cisplatin and vinblastine.

EXAMPLE

We tested IL-20 in a HeLa299 cytotoxicity assay to measure the ability of IL-20 to prevent cells from growing during normal growth conditions. We used MTT reagent (Promega, Madison, USA) as our detection and readout for this cell inhibition assay. Procedure of a cytoxicity assay:

Day 1—Plate cells out in complete growth media (with serum) at 5000 cells/well in a 96 well format and let them incubate overnight at 37 degrees and 5% CO2.

Day 2—Dump off media and add a dose response of appropriate ligands in complete growth media (IL-20, zmda1, and MDA7 at 10, 100, and 1000 ng/ml.), along with a positive control retinoic acid (100 uM) in complete growth media, while leaving some wells in complete growth media as controls of how the cells normally grow under normal conditions. Put the cells in incubator and let the assay go for 72 hrs.

Day 5—Add 15 ul/well of MTT reagent, let cells inc. for 4 hrs., then add 100 ul of stop solution, let cells inc. for an additional 1 hr., then read the plate on a multilabel counter (Victor2, PerkinElmer Life Sciences Inc., Boston). The MTT protocol will give you two readings, one at a 650 wavelength (background) and one at a 572 wavelength. Subtract the 650 reading from the 572 reading to get your actual output. These numbers are averaged and converted to a % inhibition value.

RESULTS

Retnoic acid gave a 53% inhibition of growth (positive control)

IL-20 gave a maximal 20% inhibition of growth

---

What is claimed is:

1. A method for inhibiting the growth and or proliferation of cervical cancer cells comprising bringing an Interleukin-20 (IL-20) polypeptide into contact with the cervical cancer cells.

2. The method of claim 1, wherein the cervical cancer cells are treated with radiation in conjunction with the IL-20 polypeptide.

3. The method of claim 1, wherein the cervical cancer cells are treated with one or more chemotherapeutic agents in conjunction with the IL-20 polypeptide.

4. The method of claim 3, wherein the chemotherapeutic agent is selected from the group consisting of bleomycin, chlorambucil, epirubicin, 5-fluorouracil, ifosfamide, mitomycin, methotrexate, vincristine, cisplatin and vinblastine.

5. A method for inhibiting the growth and or proliferation of cervical cancer cells comprising bringing a polypeptide comprising amino acid residues 33-176 of SEQ ID NO:2 into contact with the cervical cancer cells.

6. The method of claim 5, wherein the cervical cancer cells are treated with radiation in conjunction with the polypeptide.

7. The method of claim 5, wherein the cervical cancer cells are treated with one or more chemotherapeutic agents in conjunction with the polypeptide.

8. The method of claim 7, wherein the chemotherapeutic agent is selected from the group consisting of bleomycin, chlorambucil, epirubicin, 5-fluorouracil, ifosfamide, mitomycin, methotrexate, vincristine, cisplatin and vinblastine.

9. The method of claim 5, wherein the polypeptide comprises amino acid residues 25-176 of SEQ ID NO:2.

10. The method of claim 5, wherein the polypeptide comprises amino acid residues 1-176 of SEQ ID NO:2.

11. A method for inhibiting the growth and or proliferation of cervical cancer cells comprising bringing a polypeptide comprising amino acid residues 25-151 of SEQ ID NO:4 into contact with the cervical cancer cells.

12. The method of claim 10, wherein the cervical cancer cells are treated with radiation in conjunction with the polypeptide.

13. The method of claim 10, wherein the cervical cancer cells are treated with one or more chemotherapeutic agents in conjunction with the polypeptide.

14. The method of claim 12, wherein the chemotherapeutic agent is selected from the group consisting of bleomycin, chlorambucil, epirubicin, 5-fluorouracil, ifosfamide, mitomycin, methotrexate, vincristine, cisplatin and vinblastine.

15. The method of claim 10, wherein the polypeptide comprises amino acid residues 1-151 of SEQ ID NO:4.

* * * * *

UNITED STATES PATENT AND TRADEMARK OFFICE
CERTIFICATE OF CORRECTION

PATENT NO. : 7,582,287 B2
APPLICATION NO. : 10/321163
DATED : September 1, 2009
INVENTOR(S) : Chandrasekher et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 863 days.

Signed and Sealed this

Fourteenth Day of September, 2010

David J. Kappos
*Director of the United States Patent and Trademark Office*

SEQUENCE LISTING

```
<160> NUMBER OF SEQ ID NOS: 43

<210> SEQ ID NO 1
<211> LENGTH: 926
<212> TYPE: DNA
<213> ORGANISM: Homo sapiens
<220> FEATURE:
<221> NAME/KEY: CDS
<222> LOCATION: (45)...(572)

<400> SEQUENCE: 1
ctttgaattc ctagctcctg tggtctccag atttcaggcc taag atg aaa gcc tct      56
                                                Met Lys Ala Ser
                                                  1 agt ctt gcc ttc agc ctt ctc tct gct gcg ttt tat ctc cta tgg act     104
```

-continued

```
cct tcc act gga ctg aag aca ctc aat ttg gga agc tgt gtg atc gcc      152
Pro Ser Thr Gly Leu Lys Thr Leu Asn Leu Gly Ser Cys Val Ile Ala
             25                  30                  35 aca aac ctt cag gaa ata cga aat gga ttt tct gac ata cgg ggc agt      200
Thr Asn Leu Gln Glu Ile Arg Asn Gly Phe Ser Asp Ile Arg Gly Ser
     40                  45                  50 gtg caa gcc aaa gat gga aac att gac atc aga atc tta agg agg act      248
Val Gln Ala Lys Asp Gly Asn Ile Asp Ile Arg Ile Leu Arg Arg Thr
             55                  60                  65 gag tct ttg caa gac aca aag cct gcg aat cga tgc tgc ctc ctg cgc      296
Glu Ser Leu Gln Asp Thr Lys Pro Ala Asn Arg Cys Cys Leu Leu Arg
     70                  75                  80 cat ttg cta aga ctc tat ctg gac agg gta ttt aaa aac tac cag acc      344
His Leu Leu Arg Leu Tyr Leu Asp Arg Val Phe Lys Asn Tyr Gln Thr
             85                  90                  95                 100 cct gac cat tat act ctc cgg aag atc agc agc ctc gcc aat tcc ttt      392
Pro Asp His Tyr Thr Leu Arg Lys Ile Ser Ser Leu Ala Asn Ser Phe
                 105                 110                 115 ctt acc atc aag aag gac ctc cgg ctc tgt cat gcc cac atg aca tgc      440
Leu Thr Ile Lys Lys Asp Leu Arg Leu Cys His Ala His Met Thr Cys
         120                 125                 130 cat tgt ggg gag gaa gca atg aag aaa tac agc cag att ctg agt cac      488
His Cys Gly Glu Glu Ala Met Lys Lys Tyr Ser Gln Ile Leu Ser His
     135                 140                 145 ttt gaa aag ctg gaa cct cag gca gca gtt gtg aag gct ttg ggg gaa      536
Phe Glu Lys Leu Glu Pro Gln Ala Ala Val Val Lys Ala Leu Gly Glu
 150                 155                 160 cta gac att ctt ctg caa tgg atg gag gag aca gaa taggaggaaa           582
Leu Asp Ile Leu Leu Gln Trp Met Glu Glu Thr Glu
165                 170                 175 gtgatgctgc tgctaagaat attcgaggtc aagagctcca gtcttcaata cctgcagagg    642
aggcatgacc ccaaaccacc atctctttac tgtactagtc ttgtgctggt cacagtgtat    702
cttatttatg cattacttgc ttccttgcat gattgtcttt atgcatcccc aatcttaatt    762
gagaccatac ttgtataaga ttttttgtaat atctttctgc tattggatat atttattagt   822
taatatattt atttatttt tgctattaat gtatttaatt ttttacttgg gcatgaaact     882
ttaaaaaaaa ttcacaagat tatatttata acctgactag agca                    926
```

<210> SEQ ID NO 2
<211> LENGTH: 176
<212> TYPE: PRT
<213> ORGANISM: Homo sapiens

<400> SEQUENCE: 2

```
Met Lys Ala Ser Ser Leu Ala Phe Ser Leu Leu Ser Ala Ala Phe Tyr
 1               5                  10                  15

Leu Leu Trp Thr Pro Ser Thr Gly Leu Lys Thr Leu Asn Leu Gly Ser
             20                  25                  30

Cys Val Ile Ala Thr Asn Leu Gln Glu Ile Arg Asn Gly Phe Ser Asp
         35                  40                  45

Ile Arg Gly Ser Val Gln Ala Lys Asp Gly Asn Ile Asp Ile Arg Ile
     50                  55                  60

Leu Arg Arg Thr Glu Ser Leu Gln Asp Thr Lys Pro Ala Asn Arg Cys
 65                  70                  75                  80

Cys Leu Leu Arg His Leu Leu Arg Leu Tyr Leu Asp Arg Val Phe Lys
```

-continued

```
                        85                  90                  95
Asn Tyr Gln Thr Pro Asp His Tyr Thr Leu Arg Lys Ile Ser Ser Leu
                100                 105                 110

Ala Asn Ser Phe Leu Thr Ile Lys Lys Asp Leu Arg Leu Cys His Ala
            115                 120                 125

His Met Thr Cys His Cys Gly Glu Glu Ala Met Lys Lys Tyr Ser Gln
        130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                165                 170                 175

<210> SEQ ID NO 3
<211> LENGTH: 793
<212> TYPE: DNA
<213> ORGANISM: Homo sapiens
<220> FEATURE:
<221> NAME/KEY: CDS
<222> LOCATION: (45)...(497)

<400> SEQUENCE: 3
ctttgaattc ctagctcctg tggtctccag atttcaggcc taag atg aaa gcc tct       56
                                                Met Lys Ala Ser
                                                  1 agt ctt gcc ttc agc ctt ctc tct gct gcg ttt tat ctc cta tgg act      104
Ser Leu Ala Phe Ser Leu Leu Ser Ala Ala Phe Tyr Leu Leu Trp Thr
  5                  10                  15                  20 cct tcc act gga ctg aag aca ctc aat ttg gga agc tgt gtg atc gcc      152
Pro Ser Thr Gly Leu Lys Thr Leu Asn Leu Gly Ser Cys Val Ile Ala
             25                  30                  35 aca aac ctt cag gaa ata cga aat gga ttt tct gac ata cgg ggc agt      200
Thr Asn Leu Gln Glu Ile Arg Asn Gly Phe Ser Asp Ile Arg Gly Ser
         40                  45                  50 gtg caa gcc aaa gat gga aac att gac atc aga atc tta agg agg act      248
Val Gln Ala Lys Asp Gly Asn Ile Asp Ile Arg Ile Leu Arg Arg Thr
     55                  60                  65 gag tct ttg caa gac aca aag cct gcg aat cga tgc tgc ctc ctg cgc      296
Glu Ser Leu Gln Asp Thr Lys Pro Ala Asn Arg Cys Cys Leu Leu Arg
 70                  75                  80 cat ttg cta aga ctc tat ctg gac agg gta ttt aaa aac tac cag acc      344
His Leu Leu Arg Leu Tyr Leu Asp Arg Val Phe Lys Asn Tyr Gln Thr
 85                  90                  95                 100 cct gac cat tat act ctc cgg aag atc agc agc ctc gcc aat tcc ttt      392
Pro Asp His Tyr Thr Leu Arg Lys Ile Ser Ser Leu Ala Asn Ser Phe
                105                 110                 115 ctt acc atc aag aag gac ctc cgg ctc tgt ctg gaa cct cag gca gca      440
Leu Thr Ile Lys Lys Asp Leu Arg Leu Cys Leu Glu Pro Gln Ala Ala
            120                 125                 130 gtt gtg aag gct ttg ggg gaa cta gac att ctt ctg caa tgg atg gag      488
Val Val Lys Ala Leu Gly Glu Leu Asp Ile Leu Leu Gln Trp Met Glu
        135                 140                 145 gag aca gaa taggaggaaa gtgatgctgc tgctaagaat attcgaggtc              537
Glu Thr Glu
    150 aagagctcca gtcttcaata cctgcagagg aggcatgacc ccaaaccacc atctctttac   597 tgtactagtc ttgtgctggt cacagtgtat cttatttatg cattacttgc ttccttgcat   657 gattgtcttt atgcatcccc aatcttaatt gagaccatac ttgtataaga ttttttgtaat   717 atctttctgc tattggatat attttattagt taatatattt atttatttttt tgctattaat  777
```
gtatttaatt ttttac                                                    793

<210> SEQ ID NO 4
<211> LENGTH: 151
<212> TYPE: PRT
<213> ORGANISM: Homo sapiens

<400> SEQUENCE: 4

Met Lys Ala Ser Ser Leu Ala Phe Ser Leu Ser Ala Ala Phe Tyr
 1               5                  10                  15

Leu Leu Trp Thr Pro Ser Thr Gly Leu Lys Thr Leu Asn Leu Gly Ser
            20                  25                  30

Cys Val Ile Ala Thr Asn Leu Gln Glu Ile Arg Asn Gly Phe Ser Asp
        35                  40                  45

Ile Arg Gly Ser Val Gln Ala Lys Asp Gly Asn Ile Asp Ile Arg Ile
    50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                85                  90                  95

Asn Tyr Gln Thr Pro Asp His Tyr Thr Leu Arg Lys Ile Ser Ser Leu
            100                 105                 110

Ala Asn Ser Phe Leu Thr Ile Lys Lys Asp Leu Arg Leu Cys Leu Glu
        115                 120                 125

Pro Gln Ala Ala Val Val Lys Ala Leu Gly Leu Asp Ile Leu Leu
    130                 135                 140

Gln Trp Met Glu Glu Thr Glu
145                 150

<210> SEQ ID NO 5
<211> LENGTH: 253
<212> TYPE: DNA
<213> ORGANISM: Homo sapiens

<400> SEQUENCE: 5
ctttgaattc ctagctcctg tggtctccag atttcaggcc taagatgaaa gcctctagtc    60
ttgccttcag ccttctctct gctgcgtttt atctcctatg gactccttcc actggactga   120
agacactcaa tttgggaagc tgtgtgatcg ccacaaacct tcaggaaata cgaaatggat   180
tttctgagat acggggcagt gtgcaagcca aagatggaaa cattgacatc agaatcttaa   240
ggaggactga gtc                                                      253

<210> SEQ ID NO 6
<211> LENGTH: 24
<212> TYPE: DNA
<213> ORGANISM: Homo sapiens

<400> SEQUENCE: 6
attcctagct cctgtggtct ccag                                           24

<210> SEQ ID NO 7
<211> LENGTH: 25
<212> TYPE: DNA
<213> ORGANISM: Homo sapiens

<400> SEQUENCE: 7
ctctgctgcg ttttatctcc tatgg                                          25

<210> SEQ ID NO 8
<211> LENGTH: 22
<212> TYPE: DNA
<213> ORGANISM: Homo sapiens

<400> SEQUENCE: 8
tcccaaattg agtgtcttca gt                                              22

<210> SEQ ID NO 9
<211> LENGTH: 45
<212> TYPE: DNA
<213> ORGANISM: Homo sapiens

<400> SEQUENCE: 9
cacagcttcc caaattgagt gtcttcagtc cagtggaagg agtcc                     45

<210> SEQ ID NO 10
<211> LENGTH: 747
<212> TYPE: DNA
<213> ORGANISM: Homo sapiens

<400> SEQUENCE: 10
ttttctgaca tacggggcag tgtgcaagcc aaagatggaa acattgacat cagaatctta     60
aggaggactg agtctttgca agacacaaag cctgcgaatc gatgctgcct cctgcgccat    120
ttgctaagac tctatctgga cagggtattt aaaaactacc agacccctga ccattatact    180
ctccggaaga tcagcagcct cgccaattcc tttcttacca tcaagaagga cctccggctc    240
tgtcatgccc acatgacatg ccattgtggg gaggaagcaa tgaagaaata cagccagatt    300
ctgagtcact ttgaaaagct ggaacctcag gcagcagttg tgaaggcttt gggggaacta    360
gacattcttc tgcaatggat ggaggagaca gaataggagg aaagtgatgc tgctgctaag    420
aatattcgag gtcaagagct ccagtcttca atacctgcag aggaggcatg accccaaacc    480
accatctctt tactgtacta gtcttgtgct ggtcacagtg tatcttattt atgcattact    540
tgcttccttg catgattgtc tttatgcatc cccaatctta attgagacca tacttgtata    600
agatttttgt aatatctttc tgctattgga tatatttatt agttaatata tttatttatt    660
ttttgctatt aatgtatttta attttttact tgggcatgaa actttaaaaa aaattcacaa    720
gattatattt ataacctgac tagagca                                        747

<210> SEQ ID NO 11
<211> LENGTH: 614
<212> TYPE: DNA
<213> ORGANISM: Homo sapiens

<400> SEQUENCE: 11
ttttctgaca tacggggcag tgtgcaagcc aaagatggaa acattgacat cagaatctta     60
aggaggactg agtctttgca agacacaaag cctgcgaatc gatgctgcct cctgcgccat    120
ttgctaagac tctatctgga cagggtattt aaaaactacc agacccctga ccattatact    180
ctccggaaga tcagcagcct cgccaattcc tttcttacca tcaagaagga cctccggctc    240
tgtctggaac tcaggcagc agttgtgaag ctttggggg aactagacat tcttctgcaa     300
tggatggagg agacagaata ggaggaaagt gatgctgctg ctaagaatat cgaggtcaa    360 gagctccagt cttcaatacc tgcagaggag gcatgacccc aaaccaccat ctctttactg    420
tactagtctt gtgctggtca cagtgtatct tatttatgca ttacttgctt ccttgcatga    480
ttgtctttat gcatccccaa tcttaattga gaccatactt gtataagatt tttgtaatat    540

-continued

```
ctttctgcta ttggatatat ttattagtta atatatttat ttatttttg ctattaatgt      600 atttaattt ttac                                                        614
```

<210> SEQ ID NO 12
<211> LENGTH: 152
<212> TYPE: PRT
<213> ORGANISM: Homo sapiens

<400> SEQUENCE: 12

```
Leu Lys Thr Leu Asn Leu Gly Ser Cys Val Ile Ala Thr Asn Leu Gln
  1               5                  10                  15

Glu Ile Arg Asn Gly Phe Ser Asp Ile Arg Gly Ser Val Gln Ala Lys
             20                  25                  30

Asp Gly Asn Ile Asp Ile Arg Ile Leu Arg Arg Thr Glu Ser Leu Gln
         35                  40                  45

Asp Thr Lys Pro Ala Asn Arg Cys Cys Leu Leu Arg His Leu Leu Arg
     50                  55                  60

Leu Tyr Leu Asp Arg Val Phe Lys Asn Tyr Gln Thr Pro Asp His Tyr
 65                  70                  75                  80

Thr Leu Arg Lys Ile Ser Ser Leu Ala Asn Ser Phe Leu Thr Ile Lys
                 85                  90                  95

Lys Asp Leu Arg Leu Cys His Ala His Met Thr Cys His Cys Gly Glu
            100                 105                 110

Glu Ala Met Lys Lys Tyr Ser Gln Ile Leu Ser His Phe Glu Lys Leu
        115                 120                 125

Glu Pro Gln Ala Ala Val Val Lys Ala Leu Gly Glu Leu Asp Ile Leu
    130                 135                 140

Leu Gln Trp Met Glu Glu Thr Glu
145                 150
```

<210> SEQ ID NO 13
<211> LENGTH: 127
<212> TYPE: PRT
<213> ORGANISM: Homo sapiens

<400> SEQUENCE: 13

```
Leu Lys Thr Leu Asn Leu Gly Ser Cys Val Ile Ala Thr Asn Leu Gln
  1               5                  10                  15

Glu Ile Arg Asn Gly Phe Ser Asp Ile Arg Gly Ser Val Gln Ala Lys
             20                  25                  30

Asp Gly Asn Ile Asp Ile Arg Ile Leu Arg Arg Thr Glu Ser Leu Gln
         35                  40                  45

Asp Thr Lys Pro Ala Asn Arg Cys Cys Leu Leu Arg His Leu Leu Arg
     50                  55                  60

Leu Tyr Leu Asp Arg Val Phe Lys Asn Tyr Gln Thr Pro Asp His Tyr
 65                  70                  75                  80

Thr Leu Arg Lys Ile Ser Ser Leu Ala Asn Ser Phe Leu Thr Ile Lys
                 85                  90                  95

Lys Asp Leu Arg Leu Cys Leu Glu Pro Gln Ala Ala Val Val Lys Ala
            100                 105                 110

Leu Gly Glu Leu Asp Ile Leu Leu Gln Trp Met Glu Glu Thr Glu
        115                 120                 125
```

<210> SEQ ID NO 14
<211> LENGTH: 15
<212> TYPE: PRT

<210> SEQ ID NO 15
<211> LENGTH: 15
<212> TYPE: PRT
<213> ORGANISM: Homo sapiens

<400> SEQUENCE: 15

Leu Asp Arg Val Phe Lys Asn Tyr Gln Thr Pro Asp His Tyr Thr
1               5                   10                  15

<210> SEQ ID NO 16
<211> LENGTH: 15
<212> TYPE: PRT
<213> ORGANISM: Homo sapiens

<400> SEQUENCE: 16

Leu Ala Asn Ser Phe Leu Thr Ile Lys Lys Asp Leu Arg Leu Cys
1               5                   10                  15

<210> SEQ ID NO 17
<211> LENGTH: 15
<212> TYPE: PRT
<213> ORGANISM: Homo sapiens

<400> SEQUENCE: 17

Val Val Lys Ala Leu Gly Glu Leu Asp Ile Leu Leu Gln Trp Met
1               5                   10                  15

<210> SEQ ID NO 18
<211> LENGTH: 824
<212> TYPE: DNA
<213> ORGANISM: Mus musculus
<220> FEATURE:
<221> NAME/KEY: CDS
<222> LOCATION: (71)...(598)

<400> SEQUENCE: 18
tgggagacat cgatagccct gattgatctc tttgaatttt cgcttctggt ctccaggatc    60
taggtgtaag atg aaa ggc ttt ggt ctt gcc ttt gga ctg ttc tcc gct       109
        Met Lys Gly Phe Gly Leu Ala Phe Gly Leu Phe Ser Ala
            1               5                   10 gtg ggt ttt ctt ctc tgg act cct tta act ggg ctc aag acc ctc cat      157
Val Gly Phe Leu Leu Trp Thr Pro Leu Thr Gly Leu Lys Thr Leu His
    15                  20                  25 ttg gga agc tgt gtg att act gca aac cta cag gca ata caa aag gaa      205
Leu Gly Ser Cys Val Ile Thr Ala Asn Leu Gln Ala Ile Gln Lys Glu
30                  35                  40                  45 ttt tct gag att cgg gat agt gtg caa gct gaa gat aca aat att gac      253
Phe Ser Glu Ile Arg Asp Ser Val Gln Ala Glu Asp Thr Asn Ile Asp
                50                  55                  60 atc aga att tta agg acg act gag tct ttg aaa gac ata aag tct ttg      301
Ile Arg Ile Leu Arg Thr Thr Glu Ser Leu Lys Asp Ile Lys Ser Leu
            65                  70                  75 gat agg tgc tgc ttc ctt cgt cat cta gtg aga ttc tat ctg gac agg      349
Asp Arg Cys Cys Phe Leu Arg His Leu Val Arg Phe Tyr Leu Asp Arg
        80                  85                  90 gta ttc aaa gtc tac cag acc cct gac cac cat acc ctg aga aag atc      397
Val Phe Lys Val Tyr Gln Thr Pro Asp His His Thr Leu Arg Lys Ile

```
                 95                  100                 105
agc agc ctc gcc aac tcc ttt ctt atc atc aag aag gac ctc tca gtc    445
Ser Ser Leu Ala Asn Ser Phe Leu Ile Ile Lys Lys Asp Leu Ser Val
110             115                 120                 125 tgt cat tct cac atg gca tgt cat tgt ggg gaa gaa gca atg gag aaa    493
Cys His Ser His Met Ala Cys His Cys Gly Glu Glu Ala Met Glu Lys
                130                 135                 140 tac aac caa att ctg agt cac ttc ata gag ttg gaa ctt cag gca gcg    541
Tyr Asn Gln Ile Leu Ser His Phe Ile Glu Leu Glu Leu Gln Ala Ala
                145                 150                 155 gtg gta aag gct ttg gga gaa cta ggc att ctt ctg aga tgg atg gag    589
Val Val Lys Ala Leu Gly Glu Leu Gly Ile Leu Leu Arg Trp Met Glu
                160                 165                 170 gag atg cta tagatgaaag tggagaggct gctgagaaca ctcctgtcca            638
Glu Met Leu
        175 agaatctcag acctcagcac catgaagaca tggccccagg tgctggcatt tctactcaag  698 agttccagtc ctcagcacca cgaagatggc ctcaaaccac cacccctttg tgatataact  758 tagtgctagc tatgtgtata ttatttctac attattggct cccttatgtg aatgccttca  818 tgtgtc                                                              824
```

<210> SEQ ID NO 19
<211> LENGTH: 176
<212> TYPE: PRT
<213> ORGANISM: Mus musculus

<400> SEQUENCE: 19

```
Met Lys Gly Phe Gly Leu Ala Phe Gly Leu Phe Ser Ala Val Gly Phe
1               5                   10                  15

Leu Leu Trp Thr Pro Leu Thr Gly Leu Lys Thr Leu His Leu Gly Ser
            20                  25                  30

Cys Val Ile Thr Ala Asn Leu Gln Ala Ile Gln Lys Glu Phe Ser Glu
        35                  40                  45

Ile Arg Asp Ser Val Gln Ala Glu Asp Thr Asn Ile Asp Ile Arg Ile
    50                  55                  60

Leu Arg Thr Thr Glu Ser Leu Lys Asp Ile Lys Ser Leu Asp Arg Cys
65                  70                  75                  80

Cys Phe Leu Arg His Leu Val Arg Phe Tyr Leu Asp Arg Val Phe Lys
                85                  90                  95

Val Tyr Gln Thr Pro Asp His His Thr Leu Arg Lys Ile Ser Ser Leu
            100                 105                 110

Ala Asn Ser Phe Leu Ile Ile Lys Lys Asp Leu Ser Val Cys His Ser
        115                 120                 125

His Met Ala Cys His Cys Gly Glu Glu Ala Met Glu Lys Tyr Asn Gln
    130                 135                 140

Ile Leu Ser His Phe Ile Glu Leu Glu Leu Gln Ala Ala Val Val Lys
145                 150                 155                 160

Ala Leu Gly Glu Leu Gly Ile Leu Leu Arg Trp Met Glu Glu Met Leu
                165                 170                 175
```

<210> SEQ ID NO 20
<211> LENGTH: 152
<212> TYPE: PRT
<213> ORGANISM: Mus musculus

<400> SEQUENCE: 20

```
Leu Lys Thr Leu His Leu Gly Ser Cys Val Ile Thr Ala Asn Leu Gln
 1               5                  10                  15

Ala Ile Gln Lys Glu Phe Ser Glu Ile Arg Asp Ser Val Gln Ala Glu
             20                  25                  30

Asp Thr Asn Ile Asp Ile Arg Ile Leu Arg Thr Thr Glu Ser Leu Lys
         35                  40                  45

Asp Ile Lys Ser Leu Asp Arg Cys Cys Phe Leu Arg His Leu Val Arg
     50                  55                  60

Phe Tyr Leu Asp Arg Val Phe Lys Val Tyr Gln Thr Pro Asp His His
 65                  70                  75                  80

Thr Leu Arg Lys Ile Ser Ser Leu Ala Asn Ser Phe Leu Ile Ile Lys
                 85                  90                  95

Lys Asp Leu Ser Val Cys His Ser His Met Ala Cys His Cys Gly Glu
             100                 105                 110

Glu Ala Met Glu Lys Tyr Asn Gln Ile Leu Ser His Phe Ile Glu Leu
         115                 120                 125

Glu Leu Gln Ala Ala Val Val Lys Ala Leu Gly Glu Leu Gly Ile Leu
     130                 135                 140

Leu Arg Trp Met Glu Met Leu
145                 150

<210> SEQ ID NO 21
<211> LENGTH: 16
<212> TYPE: PRT
<213> ORGANISM: Mus musculus

<400> SEQUENCE: 21

Ile Thr Ala Asn Leu Gln Ala Ile Gln Lys Glu Phe Ser Glu Ile Arg
 1               5                  10                  15

<210> SEQ ID NO 22
<211> LENGTH: 15
<212> TYPE: PRT
<213> ORGANISM: Mus musculus

<400> SEQUENCE: 22

Leu Asp Arg Val Phe Lys Val Tyr Gln Thr Pro Asp His His Thr
 1               5                  10                  15

<210> SEQ ID NO 23
<211> LENGTH: 15
<212> TYPE: PRT
<213> ORGANISM: Mus musculus

<400> SEQUENCE: 23

Leu Ala Asn Ser Phe Leu Ile Ile Lys Lys Asp Leu Ser Val Cys
 1               5                  10                  15

<210> SEQ ID NO 24
<211> LENGTH: 15
<212> TYPE: PRT
<213> ORGANISM: Mus muculus

<400> SEQUENCE: 24

Val Val Lys Ala Leu Gly Glu Leu Gly Ile Leu Leu Arg Trp Met
 1               5                  10                  15

<210> SEQ ID NO 25
<211> LENGTH: 144
<212> TYPE: PRT
<213> ORGANISM: Mus muculus
```

<400> SEQUENCE: 25

Cys Val Ile Thr Ala Asn Leu Gln Ala Ile Gln Lys Glu Phe Ser Glu
1               5                   10                  15

Ile Arg Asp Ser Val Gln Ala Glu Asp Thr Asn Ile Asp Ile Arg Ile
                20                  25                  30

Leu Arg Thr Thr Glu Ser Leu Lys Asp Ile Lys Ser Leu Asp Arg Cys
            35                  40                  45

Cys Phe Leu Arg His Leu Val Arg Phe Tyr Leu Asp Arg Val Phe Lys
50                  55                  60

Val Tyr Gln Thr Pro Asp His His Thr Leu Arg Lys Ile Ser Ser Leu
65                  70                  75                  80

Ala Asn Ser Phe Leu Ile Ile Lys Lys Asp Leu Ser Val Cys His Ser
                85                  90                  95

His Met Ala Cys His Cys Gly Glu Glu Ala Met Glu Lys Tyr Asn Gln
            100                 105                 110

Ile Leu Ser His Phe Ile Glu Leu Glu Leu Gln Ala Ala Val Val Lys
            115                 120                 125

Ala Leu Gly Glu Leu Gly Ile Leu Leu Arg Trp Met Glu Glu Met Leu
130                 135                 140

<210> SEQ ID NO 26
<211> LENGTH: 144
<212> TYPE: PRT
<213> ORGANISM: Homo sapiens

<400> SEQUENCE: 26

Cys Val Ile Ala Thr Asn Leu Gln Glu Ile Arg Asn Gly Phe Ser Asp
1               5                   10                  15

Ile Arg Gly Ser Val Gln Ala Lys Asp Gly Asn Ile Asp Ile Arg Ile
                20                  25                  30

Leu Arg Arg Thr Glu Ser Leu Gln Asp Thr Lys Pro Ala Asn Arg Cys
            35                  40                  45

Cys Leu Leu Arg His Leu Leu Arg Leu Tyr Leu Asp Arg Val Phe Lys
50                  55                  60

Asn Tyr Gln Thr Pro Asp His Tyr Thr Leu Arg Lys Ile Ser Ser Leu
65                  70                  75                  80

Ala Asn Ser Phe Leu Thr Ile Lys Lys Asp Leu Arg Leu Cys His Ala
                85                  90                  95

His Met Thr Cys His Cys Gly Glu Glu Ala Met Lys Lys Tyr Ser Gln
            100                 105                 110

Ile Leu Ser His Phe Glu Lys Leu Glu Pro Gln Ala Ala Val Val Lys
            115                 120                 125

Ala Leu Gly Glu Leu Asp Ile Leu Leu Gln Trp Met Glu Glu Thr Glu
130                 135                 140

<210> SEQ ID NO 27
<211> LENGTH: 38
<212> TYPE: PRT
<213> ORGANISM: Homo sapiens

<400> SEQUENCE: 27

Cys Gly Glu Glu Ala Met Lys Lys Tyr Ser Gln Ile Leu Ser His Phe
1               5                   10                  15

Glu Lys Leu Glu Pro Gln Ala Ala Val Val Lys Ala Leu Gly Glu Leu
                20                  25                  30

```
Asp Ile Leu Leu Gln Trp
        35

<210> SEQ ID NO 28
<211> LENGTH: 71
<212> TYPE: PRT
<213> ORGANISM: Homo sapiens

<400> SEQUENCE: 28

Ile Ala Thr Asn Leu Gln Glu Ile Arg Asn Gly Phe Ser Asp Ile Arg
1               5                   10                  15

Gly Ser Val Gln Ala Lys Asp Gly Asn Ile Asp Ile Arg Ile Leu Arg
            20                  25                  30

Arg Thr Glu Ser Leu Gln Asp Thr Lys Pro Ala Asn Arg Cys Cys Leu
        35                  40                  45

Leu Arg His Leu Leu Arg Leu Tyr Leu Asp Arg Val Phe Lys Asn Tyr
    50                  55                  60

Gln Thr Pro Asp His Tyr Thr
65                  70

<210> SEQ ID NO 29
<211> LENGTH: 92
<212> TYPE: PRT
<213> ORGANISM: Homo sapiens

<400> SEQUENCE: 29

Ile Ala Thr Asn Leu Gln Glu Ile Arg Asn Gly Phe Ser Asp Ile Arg
1               5                   10                  15

Gly Ser Val Gln Ala Lys Asp Gly Asn Ile Asp Ile Arg Ile Leu Arg
            20                  25                  30

Arg Thr Glu Ser Leu Gln Asp Thr Lys Pro Ala Asn Arg Cys Cys Leu
        35                  40                  45

Leu Arg His Leu Leu Arg Leu Tyr Leu Asp Arg Val Phe Lys Asn Tyr
    50                  55                  60

Gln Thr Pro Asp His Tyr Thr Leu Arg Lys Ile Ser Ser Leu Ala Asn
65                  70                  75                  80

Ser Phe Leu Thr Ile Lys Lys Asp Leu Arg Leu Cys
                85                  90

<210> SEQ ID NO 30
<211> LENGTH: 82
<212> TYPE: PRT
<213> ORGANISM: Homo sapiens

<400> SEQUENCE: 30

Leu Asp Arg Val Phe Lys Asn Tyr Gln Thr Pro Asp His Tyr Thr Leu
1               5                   10                  15

Arg Lys Ile Ser Ser Leu Ala Asn Ser Phe Leu Thr Ile Lys Lys Asp
            20                  25                  30

Leu Arg Leu Cys His Ala His Met Thr Cys His Cys Gly Glu Glu Ala
        35                  40                  45

Met Lys Lys Tyr Ser Gln Ile Leu Ser His Phe Glu Lys Leu Glu Pro
    50                  55                  60

Gln Ala Ala Val Val Lys Ala Leu Gly Glu Leu Asp Ile Leu Leu Gln
65                  70                  75                  80

Trp Met

<210> SEQ ID NO 31
```

<210> SEQ ID NO 31
<211> LENGTH: 36
<212> TYPE: PRT
<213> ORGANISM: Homo sapiens

<400> SEQUENCE: 31

Leu Asp Arg Val Phe Lys Asn Tyr Gln Thr Pro Asp His Tyr Thr Leu
1               5                   10                  15

Arg Lys Ile Ser Ser Leu Ala Asn Ser Phe Leu Thr Ile Lys Lys Asp
            20                  25                  30

Leu Arg Leu Cys
        35

<210> SEQ ID NO 32
<211> LENGTH: 61
<212> TYPE: PRT
<213> ORGANISM: Homo sapiens

<400> SEQUENCE: 32

Leu Ala Asn Ser Phe Leu Thr Ile Lys Lys Asp Leu Arg Leu Cys His
1               5                   10                  15

Ala His Met Thr Cys His Cys Gly Glu Glu Ala Met Lys Lys Tyr Ser
            20                  25                  30

Gln Ile Leu Ser His Phe Glu Lys Leu Glu Pro Gln Ala Ala Val Val
        35                  40                  45

Lys Ala Leu Gly Glu Leu Asp Ile Leu Leu Gln Trp Met
    50                  55                  60

<210> SEQ ID NO 33
<211> LENGTH: 756
<212> TYPE: DNA
<213> ORGANISM: Mus musculus
<220> FEATURE:
<221> NAME/KEY: CDS
<222> LOCATION: (71)...(532)

<400> SEQUENCE: 33
tgggagacat cgatagccct gattgatctc tttgaatttt cgcttctggt ctccaggatc      60
taggtgtaag atg aaa ggc ttt ggt ctt gcc ttt gga ctg ttc tcc gct        109
           Met Lys Gly Phe Gly Leu Ala Phe Gly Leu Phe Ser Ala
               1               5                   10 gtg ggt ttt ctt ctc tgg act cct tta act ggg ctc aag acc ctc cat      157
Val Gly Phe Leu Leu Trp Thr Pro Leu Thr Gly Leu Lys Thr Leu His
         15                  20                  25 ttg gga agc tgt gtg att act gca aac cta cag gca ata caa aag gaa      205
Leu Gly Ser Cys Val Ile Thr Ala Asn Leu Gln Ala Ile Gln Lys Glu
 30                  35                  40                  45 ttt tct gag att cgg gat agt gtg tct ttg gat agg tgc tgc ttc ctt      253
Phe Ser Glu Ile Arg Asp Ser Val Ser Leu Asp Arg Cys Cys Phe Leu
                 50                  55                  60 cgt cat cta gtg aga ttc tat ctg gac agg gta ttc aaa gtc tac cag      301
Arg His Leu Val Arg Phe Tyr Leu Asp Arg Val Phe Lys Val Tyr Gln
             65                  70                  75 acc cct gac cac cat acc ctg aga aag atc agc agc ctc gcc aac tcc      349
Thr Pro Asp His His Thr Leu Arg Lys Ile Ser Ser Leu Ala Asn Ser
         80                  85                  90 ttt ctt atc atc aag aag gac ctc tca gtc tgt cat tct cac atg gca      397
Phe Leu Ile Ile Lys Lys Asp Leu Ser Val Cys His Ser His Met Ala
     95                  100                 105 tgt cat tgt ggg gaa gaa gca atg gag aaa tac aac caa att ctg agt      445
Cys His Cys Gly Glu Glu Ala Met Glu Lys Tyr Asn Gln Ile Leu Ser
110                 115                 120                 125

```
cac ttc ata gag ttg gaa ctt cag gca gcg gtg gta aag gct ttg gga      493
His Phe Ile Glu Leu Glu Leu Gln Ala Ala Val Val Lys Ala Leu Gly
                130                 135                 140 gaa cta ggc att ctt ctg aga tgg atg gag gag atg cta tagatgaaag       542
Glu Leu Gly Ile Leu Leu Arg Trp Met Glu Glu Met Leu
            145                 150 tggataggct gctgagaaca ctcctgtcca agaatctcag acctcagcac catgaagaca    602
tggccccagg tgctggcatt tctactcaag agttccagtc ctcagcacca cgaagatggc    662
ctcaaaccac caccccttg tgatataact tagtgctagc tatgtgtata ttatttctac     722
attattggct cccttatgtg aatgccttca tgtg                                756

<210> SEQ ID NO 34
<211> LENGTH: 154
<212> TYPE: PRT
<213> ORGANISM: Mus musculus

<400> SEQUENCE: 34

Met Lys Gly Phe Gly Leu Ala Phe Gly Leu Phe Ser Ala Val Gly Phe
1               5                   10                  15

Leu Leu Trp Thr Pro Leu Thr Gly Leu Lys Thr Leu His Leu Gly Ser
                20                  25                  30

Cys Val Ile Thr Ala Asn Leu Gln Ala Ile Gln Lys Glu Phe Ser Glu
            35                  40                  45

Ile Arg Asp Ser Val Ser Leu Asp Arg Cys Cys Phe Leu Arg His Leu
        50                  55                  60

Val Arg Phe Tyr Leu Asp Arg Val Phe Lys Val Tyr Gln Thr Pro Asp
65                  70                  75                  80

His His Thr Leu Arg Lys Ile Ser Ser Leu Ala Asn Ser Phe Leu Ile
                85                  90                  95

Ile Lys Lys Asp Leu Ser Val Cys His Ser His Met Ala Cys His Cys
            100                 105                 110

Gly Glu Glu Ala Met Glu Lys Tyr Asn Gln Ile Leu Ser His Phe Ile
        115                 120                 125

Glu Leu Glu Leu Gln Ala Ala Val Val Lys Ala Leu Gly Glu Leu Gly
    130                 135                 140

Ile Leu Leu Arg Trp Met Glu Glu Met Leu
145                 150

<210> SEQ ID NO 35
<211> LENGTH: 130
<212> TYPE: PRT
<213> ORGANISM: Mus musculus

<400> SEQUENCE: 35

Leu Lys Thr Leu His Leu Gly Ser Cys Val Ile Thr Ala Asn Leu Gln
1               5                   10                  15

Ala Ile Gln Lys Glu Phe Ser Glu Ile Arg Asp Ser Val Ser Leu Asp
                20                  25                  30

Arg Cys Cys Phe Leu Arg His Leu Val Arg Phe Tyr Leu Asp Arg Val
            35                  40                  45

Phe Lys Val Tyr Gln Thr Pro Asp His His Thr Leu Arg Lys Ile Ser
        50                  55                  60

Ser Leu Ala Asn Ser Phe Leu Ile Ile Lys Lys Asp Leu Ser Val Cys
65                  70                  75                  80

His Ser His Met Ala Cys His Cys Gly Glu Glu Ala Met Glu Lys Tyr
```

```
                    85                  90                  95
Asn Gln Ile Leu Ser His Phe Ile Glu Leu Glu Leu Gln Ala Ala Val
            100                 105                 110
Val Lys Ala Leu Gly Glu Leu Gly Ile Leu Leu Arg Trp Met Glu Glu
        115                 120                 125
Met Leu
    130
```

<210> SEQ ID NO 36
<211> LENGTH: 27
<212> TYPE: DNA
<213> ORGANISM: Homo sapiens

<400> SEQUENCE: 36
agattctatc tggacagggt attcaaa                                    27

<210> SEQ ID NO 37
<211> LENGTH: 17
<212> TYPE: DNA
<213> ORGANISM: Homo sapiens

<400> SEQUENCE: 37
gcgaggctga tctttct                                               17

<210> SEQ ID NO 38
<211> LENGTH: 25
<212> TYPE: DNA
<213> ORGANISM: Mus musculis

<400> SEQUENCE: 38
tggcgaggct gctgatcttt ctcag                                      25

<210> SEQ ID NO 39
<211> LENGTH: 25
<212> TYPE: DNA
<213> ORGANISM: Mus musculis

<400> SEQUENCE: 39
ctttatgtct ttcaaagact cagtc                                      25

<210> SEQ ID NO 40
<211> LENGTH: 26
<212> TYPE: DNA
<213> ORGANISM: Mus musculis

<400> SEQUENCE: 40
catcagaatt ttaaggacga ctgagt                                     26

<210> SEQ ID NO 41
<211> LENGTH: 25
<212> TYPE: DNA
<213> ORGANISM: Mus musculis

<400> SEQUENCE: 41
ggtggtcagg ggtctggtag acttt                                      25

<210> SEQ ID NO 42
<211> LENGTH: 23
<212> TYPE: DNA
<213> ORGANISM: Mus musculis

<400> SEQUENCE: 42
ggtgcatatt cctggtggct aga                                        23

```
<210> SEQ ID NO 43
<211> LENGTH: 25
<212> TYPE: DNA
<213> ORGANISM: Mus musculis

<400> SEQUENCE: 43
attgcagtgt aagggaatac agaga                                          25
```